United States Patent [19]

Preuss

[11] 4,370,271
[45] Jan. 25, 1983

[54] PROCESS FOR THE PARTIAL REDUCTION OF C21-STEROID CARBOXYLIC ACIDS AND THEIR ESTERS TO C21-STEROID ALCOHOLS AND NEW C21-STEROID ALCOHOLS

[75] Inventor: Wolfgang Preuss, Monheim, Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 262,969

[22] Filed: May 12, 1981

[30] Foreign Application Priority Data

May 16, 1980 [AT] Austria ........................... 2628/80

[51] Int. Cl.$^3$ ................................. C07J 5/00
[52] U.S. Cl. ........................... 260/397.45; 260/397.1
[58] Field of Search ..................... 260/397.1, 397.45

[56] References Cited

U.S. PATENT DOCUMENTS 4,189,430  2/1980  Shephard .................... 260/397.45
4,290,961  9/1981  Mestroni et al. ............ 260/397.4

FOREIGN PATENT DOCUMENTS 2558077 of 1977 Fed. Rep. of Germany ... 260/397.1

OTHER PUBLICATIONS

Chemical Pharmaceutical Bulletin, Band 24, Nr. 4, Apr. 1976, Seiten 828–831, the article by Samoto et al., more specifically compound IV on p. 829.

Primary Examiner—Elbert L. Roberts
Attorney, Agent, or Firm—Hammond & Littell, Weissenberger and Muserlian

[57] ABSTRACT

A process for the partial reduction of C21-steroid carboxylic acids and their esters to C21-steroid alcohols and new C21-steroid alcohols Δ4,17(20)-C21-steroid carboxylic acids optionally containing further double bonds in the 1- and/or 9(11)-position and their esters corresponding to general formula I below

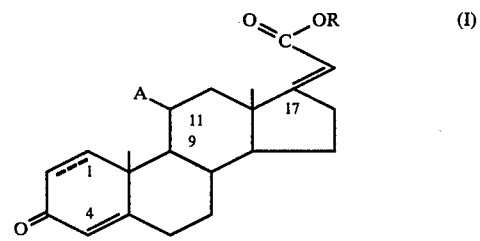

in which R represents hydrogen or a hydrocarbon radical and A represents hydrogen, hydroxyl or, together with the C-atom substituted by A, a carbonyl group and in which, finally, the substituent A may even be replaced by an additional olefinic double bond in the 9(11)-position, are reacted with diisobutyl aluminium hydride without the A-ring in the steroid skeleton being blocked in such quantities that all the oxygen-containing functional groups are reduced to the hydroxyl group. The aluminium-containing intermediate reaction product is then subjected to the selective Oppenauer oxidation to form the 3-keto compound. The 3-oxo-C21-steroid alcohols may be obtained in high yields in this way. The process is suitable for the preparation of pharmacologically active steroid compounds having the 17,21-diol-20-one configuration. It enables the new compuonds, pregna-1,4,17(20)-triene-3-one-21-ol and pregna-1,4,9(11),17(20)-tetraene-3-one-21-ol and their 21-acetoxy compounds, to be obtained.

10 Claims, No Drawings

PROCESS FOR THE PARTIAL REDUCTION OF C21-STEROID CARBOXYLIC ACIDS AND THEIR ESTERS TO C21-STEROID ALCOHOLS AND NEW C21-STEROID ALCOHOLS

This invention relates to an improved and, more particularly, simplified process for the partial reduction of the C21-carboxylic acid group in corresponding steroid carboxylic acids having a $\Delta^4$-3-one or $\Delta^{1,4}$-3-one configuration in the A-ring of the steroid skeleton to the corresponding C21-alcohol function. Although other functional groups may also be present in the steroid skeleton, they remain completely or substantially unaffected by this partial reduction.

Progesterone (4-pregnene-3,20-dione) and, in particular, progesterone derivatives having an oxygen function in the 11-position (11-oxo, 11-α-OH, 11-β-OH) corresponding to formulae (1) to (3) below

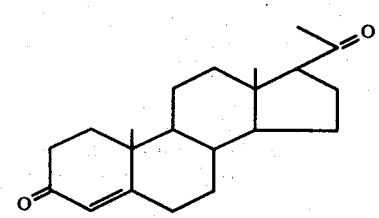

(1)

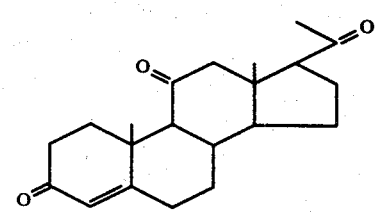

(2)

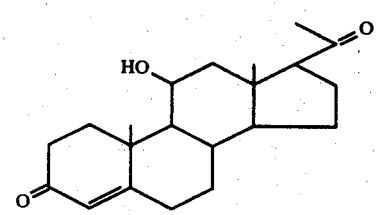

(3)

are excellent and, in some cases, commercially used starting materials for the synthesis of preliminary stages of hydrocortisone (cortisol) and, ultimately, of hydrocortisone itself. A reaction scheme on which this method is based may be found for example in L. F. Fieser, M. Fieser "Steroide (Steroids)", pages 737, 738, Verlag Chemie, Weinheim, 1961. Particulars may be found inter alia in the original literature cited therein, namely J. A. Hogg et al, J. Am. Chem. Soc. 77, 4436 (1955), and also in U.S. Pat. Nos. 2,683,724 and 2,707,184.

The reaction sequence is shown in somewhat abbreviated form in the following with reference by way of example to 11-ketoprogesterone (4):

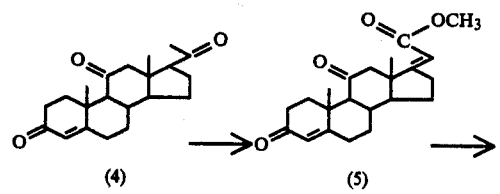

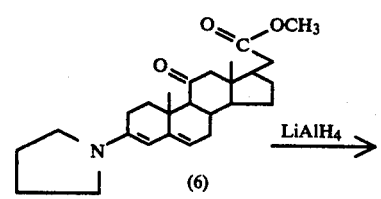

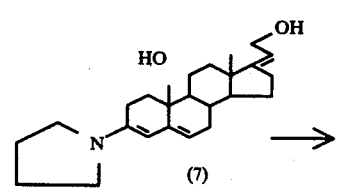

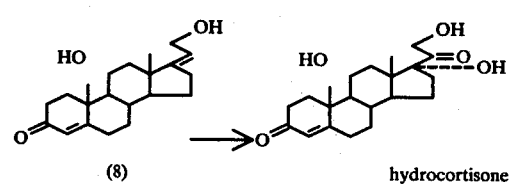

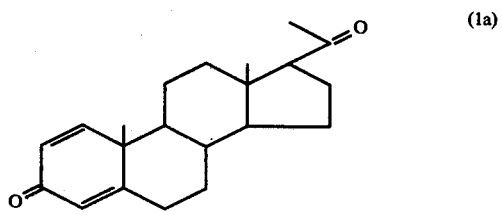

Of outstanding importance so far as the commercial usefulness of the synthesis sequence is concerned is the possibility which exists here with steroids of the progesterone type of protecting the 3-keto-4-ene system of the A-ring in the form of the enamine (7) (or even in the form of ethylene ketal) during the reduction step from (5) to (8) and, hence of avoiding over-reduction which may even readily lead to partial reduction of the double bond.

It is not possible on a commercial scale to apply this partial blocking of the A-ring to the corresponding dehydroprogesterone and comparable dehydroprogesterone derivatives. Dehydroprogesterone and its corresponding derivatives are distinguished by the 3-keto-1,4-diene structure of the A-ring, as shown in formulae (1a) to (3a) below:

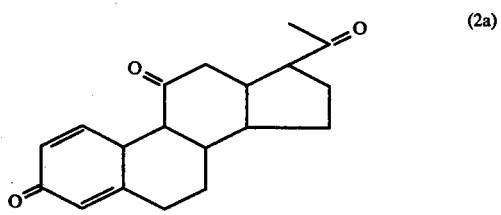

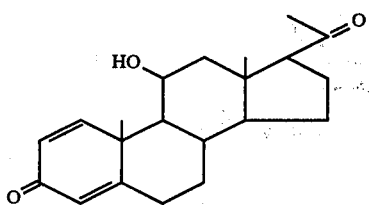

(3a)

Pregna-1,4-diene-3,20-dione (1a=dehydroprogesterone), pregna-1,4-diene-3,11,20-trione (2a) and pregna-1,4-diene-11-ol-3,20-dione (3a), which may exist both in the form of the 11-β-isomer and in the form of the 11-α-isomer, are of considerable potential importance as preliminary stages for the production of prednisolone, prednisone and other corticosteroids having a 1,4-diene-3-keto structure. Dehydroprogesterone and various derivatives thereof, including compounds (2a) and (3a) as shown above, may currently be obtained inter alia by the degradation of pregna-1,4-diene-3-one-20-carboxylic acid (Δ1,4-BNC) and/or its functional derivatives. This Δ1,4-BNC and/or its functional derivatives may be obtained microbiologically by the partial degradation of natural animal or vegetable steroid compounds, such as cholesterol or sitosterol. Applicants have already proposed numerous methods for this purpose, cf. for example European Patent Applications Nos. 004913 and 0015308.

Partial reduction of the C21 carboxylic acid group to the corresponding C21 alcohol function presents particular difficulties in the series of steroid compounds having a 1,4-diene-3-keto structure. The reason for this lies in the fact that the A-ring in compounds of the dehydroprogesterone series cannot be adequately protected.

Although J. Hogg et al. (J. Am. Soc. 77, 4438 (1955)) report that the reaction sequence previously illustrated in formula schemes (5) to (8) with reference to progesterone derivatives can be applied to the corresponding dehydroprogesterone esters having an additional 1(2)-double bond by comparison with (5), the yield which was only published considerably later (Steroids 3, 189 (1964)) amounts to only around 12% (maximum 20%) as against a yield of more than 70% for the transformation of (5) to (8).

Finally, it has recently been stated (cf. J. Fried, J. A. Edwards "Organic Reactions in Steroid Chemistry", Vol 1, pages 394-395, Van Nostrand Reinhold Company, New York 1972) that there is no useful protective group for Δ1,4-3-keto systems in steroids.

Thus, the reaction sequence illustrated for the synthesis of hydrocortisone is unsuitable for the production of preliminary stages of prednisolone in commercially viable yields from the dehydroprogesterones corresponding for example to formulae (1a) to (3a). However, a process such as this would be desirable by virtue of the fact that compounds (1a) to (3a) and other dehydroprogesterone derivatives can be obtained from Δ1,4-BNC and its compounds in conjunction with the considerable significance attributed to prednisolone, prednisone and other corticosteroids having a 1,4-diene-3-keto structure.

The object of the present invention is to provide a method by which a C21-carboxylic acid function in the C17-side chain of steroid compounds may be partly reduced, even when other, basically comparatively sensitive functional groups are present in the steroid ring skeleton. Other functional groups of the type in question are, in particular, the Δ4-3-one structure, the Δ1,4-3-one structure, other double bonds in the system, particularly in the 17(20)-position and, optionally, in the 9(11)-position and possible oxygen functions in the 11-position. With all these compounds, particular significance is attributed to starting materials which have the Δ1,4-3-one structure in the A-ring of the steroid skeleton. Another object of the invention is to enable the carboxyl group function in C21 to be partly or at least to a large extent partly reduced without any special separate protective groups having to be used for the A-ring structure.

Accordingly, the present invention relates to a process for the partial reduction of Δ4,17(20)-C21-steroid carboxylic acids optionally containing other double bonds in the 1(2)- and/or 9(11)-position and their esters corresponding to general formula I below

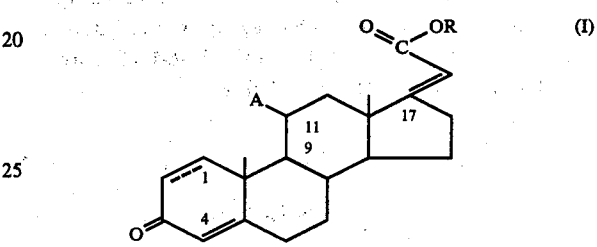

in which R represents hydrogen or a hydrocarbon radical and A represents hydrogen, hydroxyl or, together with the C-atom substituted by A, a carbonyl group and in which, finally, the substituent A may even be replaced by an additional olefinic double bond in the 9(11)-position, to C21-steroid alcohols corresponding to general formula II below

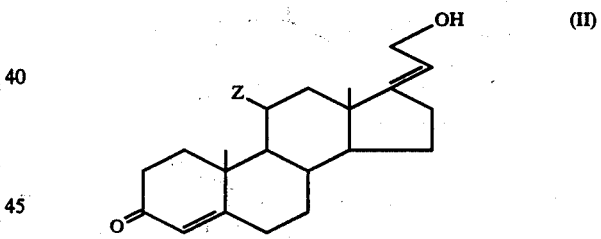

in which Z has the same meaning as A, but in this case represents hydroxyl instead of the carbonyl group. The process according to the invention is characterised in that the starting compound of general formula I which is unprotected in the A-ring of the steroid system is reacted with diisobutyl aluminium hydride (DIBAH) in such quantities that all the O-containing functional groups are reduced to the hydroxyl group, after which the aluminium-containing intermediate reaction product is subjected in known manner to the selective Oppenauer oxidation to form the 3-keto compound.

In the case of compounds corresponding to general formula I, the selective reducibility in high yields on the carboxyl group function in C21 which the invention seeks to achieve is obtained surprisingly easily using diisobutyl aluminium hydride (DIBAH) as the reducing agent. This is explained in more detail in the following with reference by way of example to the reduction of the ester (9) to the alcohol (10). The alcohol (10) itself is a new, hitherto unknown compound and falls within the scope of the invention.

Reduction is carried out in the absence of a protective group for the 1,4-diene-3-keto system of the A-ring. Instead, the reducing agent is used in a quantity sufficient to reduce both the ester group and also the 3-keto group. The double bonds of the A-ring and also the 17(20)-double bond remain unaffected.

The alkoxy aluminium derivative (11), which may be assumed as the intermediate stage, is normally not isolated, but instead is directly subjected under suitable mild conditions to a selective Oppenauer oxidation by the addition of an alcohol/ketone mixture (for example isopropanol/acetone):

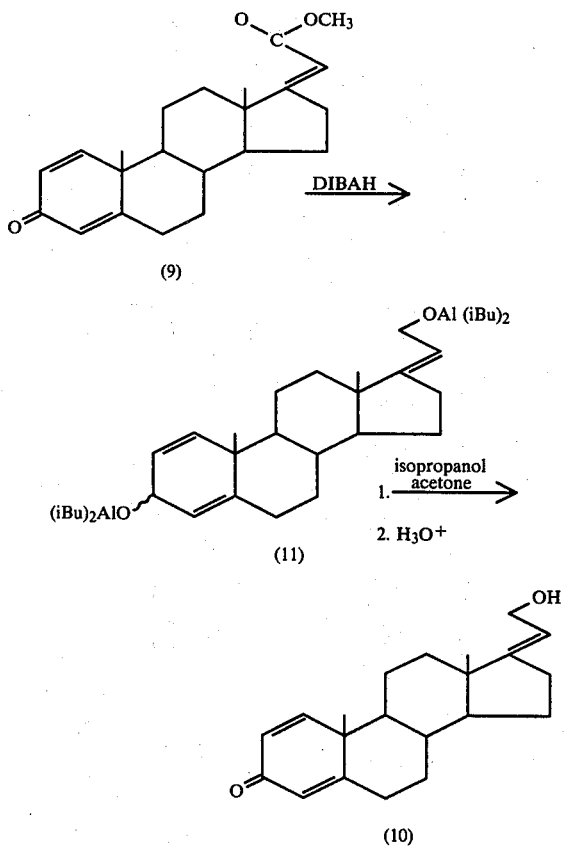

The 3-keto group is almost exclusively reformed and the C21-alcohol (10) is obtained in an isolated yield of more than 70%.

In the compounds corresponding to general formula I, R is preferably a hydrocarbon radical containing in particular no more than 20 carbon atoms and best no more than 10 carbon atoms. Aliphatic radicals, particularly aliphatic radicals containing from 1 to 5 and preferably from 1 to 3 carbon atoms, are particularly preferred. The most important radical is the methyl radical.

The partial reduction of the carboxyl or carboxylate group in C21 in accordance with the invention is also possible in the case of compounds which correspond to general formula I and which contain an additional olefinic double bond in the 9(11)-position. The same applies to compounds corresponding to general formula I in which A is a hydroxyl group in the α-position or, more particularly, in the β-position. If a carbonyl group is present in A in the starting compounds of general formula I used in accordance with the invention, i.e. if A forms a carbonyl group with the C-atom in the 11-position substituted by A, this carbonyl group is also reduced to the corresponding hydroxyl group. The 11-β-hydroxyl group formed in this case has particular significance in its own right for pharmacological reasons. Otherwise, however, what applies to all the other starting compounds of general formula I applies in this case, too, namely that the structure of the A-ring emerges unchanged from the process on completion of the two-stage reduction and selective oxidation process, this being of particular technical significance to compounds having the $\Delta^{1,4}$-3-one structure in the A-ring.

Basically, there is nothing new in the use of diisobutyl aluminium hydride as a reducing agent in steroid chemistry. It has been prescribed for certain selected steroid compounds having the 4-ene-3-keto structure. Thus, U. Eder writing in Chem. Ber. 109, 2954 (1976) describes a process for the production of testosterone from 4-androstene-3,17-dione by reduction with DIBAH, followed by selective Oppenauer oxidation. The keto group in the 17-position may be selectively reduced in this way. Transformation of the Δ4-BNC-methyl ester into the corresponding Δ4-BNC-alcohol in this way is also described. However, these known proposals use compounds which are more simple in structure than the compounds used in accordance with the invention. Thus, the starting materials used in accordance with the invention contain one double bond in the side chain but, in addition, have the Δ1,4-diene structure instead of the more simple Δ4-system in the preferred embodiment and may in addition contain an oxygen function in the 11-position or another double bond in the 9(11)-position. Because of this, it could not be predicted with any certainty that the reaction described by Eder would be applicable to the compounds used in accordance with the present invention.

An improvement in the above-described reduction of compounds corresponding to formula (5) to the diol corresponding to formula (8) by using DIBAH instead of LiAlH$_4$ is described in C.A. 63, 133367 (1965). In this case, however, the reaction in question is a reduction on a 4-ene-3-keto system protected by enamine formation—cf. formulae (6) and (7) above.

The process according to the invention is carried out as follows:

The unsaturated starting materials corresponding to general formula I which are used as starting material in the process according to the invention are obtained in high yields from the corresponding compounds of the progesterone or dehydroprogesterone type in accordance with the above general reaction scheme for the compound of formula (4) to the compound of formula (5). Particulars of this reaction may be found in the literature which has already been cited, more particularly in J. A. Hogg et al., J. Am. Chem. Soc. 77, 4436 (1955).

Reduction using diisobutyl aluminium hydride is carried out in known manner, cf. for example E. Winterfeldt in "Synthesis" 1975, pages 617 et seq.

The reaction is normally carried out at temperatures in the range from about −80° C. to +30° C., the range from −30° C. to room temperature being preferred. The temperature range from −10° to +5° C. is particularly suitable. The reaction is preferably carried out in the presence of inert solvents, for example aromatic hydrocarbons, such as toluene or benzene, although aliphatic hydrocarbons, such as hexane, or ethers, such as diethyl ether, and the like are also suitable. The reaction time is normally up to 10 hours and is preferably between 2 and 5 hours. The reaction is best carried out in an inert gas atmosphere, for example in a nitrogen atmosphere, under anhydrous conditions. It can be of advantage to add a solution of DIBAH in the inert solvent to a solution of the steroid compound in some more of the inert solvent, although the reverse procedure is also possible. The quantity in which the DIBAH is used corresponds to at least the stoichiometrically necessary quantity, although it is preferred to use a slight excess, for example a molar excess of up to 20% and preferably of up to about 10%. Reduction of the carboxyl group function in C21 requires two equivalents of DIBAH, each keto group requiring one equivalent of DIBAH.

The aluminium-containing reaction product obtained as intermedate stage does not have to be isolated for the subsequent selective Oppenauer oxidation. Instead, it is generally preferred further to work up the reduction product obtained as intermediate directly in the following Oppenauer oxidation. The Oppenauer oxidation is again carried out in accordance with the general teaching of the relevant literature, cf. for example Carl Djerassi in Organic Reactions, Vol. VI, Chapter 5 "The Oppenauer Oxidation" (J. Wiley and Sons, Inc., New York, 1951). The particular procedure adopted is as follows:

The reaction temperature is normally in the range from about 0° to 40° C., although it may even be higher. It is best to work at a temperature below 80° C. Ketone-/alcohol mixtures are used as the oxidising agent. Suitable hydride acceptors are, for example, acetone, cyclohexanone or fluorenone in admixture with isopropanol or tert.-butanol as the alcohol component. In this case, the reaction time is normally from 2 to 20 hours and preferably from 4 to 12 hours. The reaction is again carried out under anhydrous conditions.

The ketone is normally used in a large excess amounting for example to between 5 and 50 times and preferably to between 10 and 20 times the stoichiometrically necessary quantity in order to displace the equilibrium of the reaction in the required direction.

Both new compounds and compounds known per se may be obtained by the process according to the invention. Among the unsaturated alcohols of general formula II obtained in accordance with the invention, new compounds are those which have the $\Delta^{1,4}$-3-one configuration in the A-ring of the steroid skeleton and which are unsubstituted in the 11-position or even contain another double bond in the 9(11)-position. These two new C21-ol-compounds as such also form part of the present invention.

The compounds of general formula II obtained in accordance with the invention are valuable products in steroid chemistry and, more particularly, are valuable intermediate products in the preparation of pharmacologically active steroid compounds, particularly of the prednisone and/or prednisolone series. The use of the compounds of general formula II obtained in accordance with the invention for this particular purpose also falls within the scope of the present invention and is thus another subject of the technical teaching claimed herein.

To carry out this transformation of the C21-ol-compounds into products, for example of the prednisone or prednisolone series, the hydroxyl group in C21 is normally first esterified, particularly acetylated. Acetylation is carried out for example by reacting the C21-ol-compond with acetanhydride/pyridine or with acetanhydride/triethylamine/dimethylaminopyridine. Some new and some known compounds are again formed in this stage of the process. New compounds (and hence yet another part of the present invention) include the acetate of pregna-1,4,17(20)-triene-3-one-21-ol and the corresponding compounds containing an additional olefinic double bond in the 9(11)-position. Known acetates of this type are corresponding compounds having the $\Delta^4$-3-one configuration and/or an oxygen function in the 11-position.

The transformation of these compounds esterified in the C21-hydroxyl group into compounds, for example of the prednisone or prednisolone type, is carried out in known manner. Reference is made here to the already cited literature reference J. A. Hogg et al., J. Am. Chem. 77, pages 4436 et seq., particularly page 4438. More particularly, oxidative hydroxylation with osmium tetroxide takes place in this case, additional oxygen functions being introduced into C17 and C20. Where the oxidative hydroxylation step is carried out with phenyl iodosoacetate in tert.-butyl alcohol/pyridine in the presence of catalytic quantities of osmium tetroxide, hydrocortisone acetate is formed from 11-$\beta$-hydroxy-4,17(20)-pregnadiene-3-one-21-acetate and may be converted into hydrocortisone in known manner. Where starting compounds having the $\Delta$1,4-diene-3-one structure are used, compounds of the prednisone or prednisolone series are ultimately obtained.

EXAMPLE 1

Pregna-1,4,17(20)-triene-21-ol-3-one 25.4 ml of a 20% solution of diisobutyl aluminium hydride in toluene are added dropwise at 0° C. to 3 g of the ester, pregna-1,4,17(20)-cis-triene-3-one-21-acid methyl ester[1], in 60 ml of absolute toluene. After 3 hours at 0° C., first 9 ml of acetone and then 9 ml of isopropanol are added and the solution is left to return to room temperature. After standing overnight, the solution is carefully acidified at 0° C. with 10% sulfuric acid. After phase separation, the aqueous phase is extracted twice with a little methylene chloride, the organic phases are separated, washed until neutral, subsequently dried together over $Na_2SO_4$ and concentrated to dryness after the drying agent has been separated off. The residue is chromatographed over silica gel using methylene chloride/ethyl acetate (75:25). The product is obtained in a yield of 2.04 g (72%) and is shown to be pure by a thin-layer chromatogram and $^1$H-NMR spectrum.

M.p. (ether): 105°–108° C. $C_{21}H_{28}O_2$ calculated: C 80.46%, H 9.15%, observed: C 80.73%, H 9.03%.

$^1$H-NMR (80 MHz, $CDCl_3$, chemical displacement is expressed in ppm on the $\delta$-scale, based on TMS):

| | | |
|---|---|---|
| 0.96 (18-$CH_3$, s); 1.23 (19-$CH_3$, s); 4.23 (21-$CH_2$, m); | | |
| 5.32 (20-CH, m); | | |
| 6.07 | | |
| 6.15 | 6.17 | ABC-system of |
| 6.27 | 6.30 | 1-CH, 2-CH, and 4-CH |
| 6.99 | 7.11 | |

From the 17(20)-cis-configuration of the ester[1], the same configuration is also derived for the alcohol.

[1] B. J. Magerlein and J. A. Hogg, J. Amer. Chem. Soc. 80, 2220 (1958)

EXAMPLE 2

21-acetoxy-pregna-1,4,17(20)-triene-3-one 0.24 ml of acetanhydride, 0.36 ml of triethylamine and 50 mg of 4-dimethylaminopyridine are added to 400 mg of the pregna-1,4,17(20)-triene-21-ol-3-one produced in accordance with Example 1 in 10 ml of absolute methylene chloride, followed by stirring for 30 minutes at 0° C. A thin-layer chromatogram shows that the reaction is quantitative after this period. The reaction solution is successively washed with ice-cold dilute HCl, NaHCO$_3$ solution and finally with water. The CH$_2$Cl$_2$ phase is dried over Na$_2$SO$_4$, the drying agent is filtered off and the residue is concentrated to dryness. The residue is substantially pure product in a yield of more than 90%. $^1$H-NMR (80 MHz, COCl$_3$; δ-value):

0.96 (18-CH$_3$, S); 1.21 (19-CH$_3$, S); 2.01 (—$\overset{O}{\overset{\|}{C}}$—CH$_3$, S);

4.63 (21-CH$_2$, d J = 7.2 Hz); 5.24 (20-CH, m);

6.04
6.12    6.14  ⎫  ABC-system
6.23    6.25  ⎬  of 1-CH, 2-CH and 4-CH
6.98    7.08  ⎭

C$_{23}$H$_{30}$O$_3$ calculated: C 77.69%, H 8.36%; observed: C 77.93%, H 8.53%.

EXAMPLE 3

11-β-21-dihydroxy-pregna-1,4,17(20)-triene-3-one 3 g of pregna-1,4,17(20)-triene-3,11-dione-21-acid methyl ester are reduced with 32.4 ml of 20% DIBAH solution in the same way as described in Example 1. After 3 hours at 0° C., 11.1 ml of acetone and then 11.1 ml of isopropanol are added at that temperature, after which the product is left standing overnight at room temperature, heated for 1 hour to 40° C., worked up and purified in the same way as described in Example 1. 1.67 g (59%) of the alcohol are obtained:

M.p. 174°-178° C. (Lit.$^1$: 174°-175° C.).

If the ester with the Δ$^4$-A-ring is used, reduction to the alcohol with Δ$^4$-A-ring may be carried out under the same conditions and with virtually the same yield as in Example 3.

The melting point (M.p.) of the reaction product is consistent with the melting point quoted in the literature$^2$ 1. J. A. Hogg et al., J. Amer. Chem. Soc. 77, 4438 (1955)
$^2$J. A. Hogg et al., J. Amer. Chem. Soc. 77, 4436 (1955).

We claim:

1. A process for the partial reduction of Δ4,17(20)-C21-steroid carboxylic acids optionally containing further double bonds in the 1- and/or 9(11)-position and their esters corresponding to general formula I below:

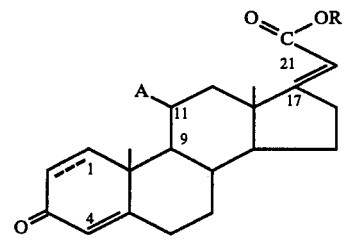

in which R represents hydrogen or a hydrocarbon radical and A represents hydrogen, hydroxyl or, together with the C-atom substituted by A, a carbonyl group and in which, the substituent A may be replaced by an additional olefinic double bond in the 9(11)-position, to C21-steroid alcohols corresponding to general formula II below:

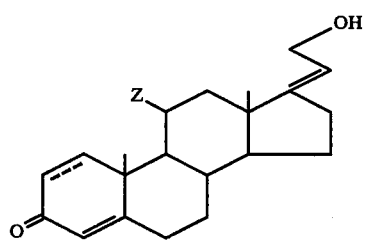

in which Z has the same meaning as A, but in this case represents hydroxyl instead of a carbonyl group, characterized in that the starting material of general formula I which is unprotected in the A-ring of the steroid ring system is reacted with diisobutyl aluminum hydride in such quantities that all the oxygen-containing functional groups are reduced to the hydroxyl group, and an intermediate Al-containing reaction product is obtained, after which said intermediate Al-containing reaction product is subjected to selective Oppenauer oxidation to form the 3-keto compound.

2. A process as claimed in claim 1, in which the reaction with diisobutyl aluminium hydride is carried out under anhydrous conditions at temperatures in the range from −80° C. to +30° C.

3. A process as claimed in claim 2 in which the reaction is carried out at a temperature in the range of −10° C. to +50° C.

4. A process as claimed in claim 1 or 2 or 3 in which the reaction is carried out in an inert solvent or solvents.

5. A process as claimed in claim 1 or 2 or 3 in which the selective Oppenauer oxidation is carried out by reacting said intermediate Al-containing reaction product obtained as intermediate stage with an isopropanol-/acetone mixture under anhydrous conditions, at temperatures below 80° C., the acetone preferably being used in a large excess over the stoichiometrically necessary quantity.

6. A process as claimed in claim 5 in which the reaction is effected at a temperature of 0° to 40° C.

7. Pregna-1,4,9(11),17(20)-tetraene-3-one-21-ol.

8. 21-acetoxy-pregna-1,4,9(11),17(20)-tetraene-3-one.

9. A process as claimed in claim 4 in which the selective Oppenauer oxidation is carried out by reacting said intermediate Al-containing reaction product obtained as intermediate stage with an isopropanol/acetone mixture under anhydrous conditions, at temperatures below 80° C., the acetone preferably being used in a large excess over the stoichiometrically necessary quantity.

10. A process as claimed in claim 9 in which the reaction is effected at a temperature of 0° to 40° C.

* * * * *